United States Patent

Chang et al.

[11] Patent Number: 5,426,055
[45] Date of Patent: Jun. 20, 1995

[54] METHOD TO DETECT LEWIS ACID DECOMPOSITION PRODUCTS IN LITHIUM SALT-CONTAINING NONAQUEOUS ELECTROLYTE

[75] Inventors: On-Kok Chang; Milton N. Golovin, both of San Jose, Calif.

[73] Assignee: Valence Technology, Inc., San Jose, Calif.

[21] Appl. No.: 77,205

[22] Filed: Feb. 22, 1994

[51] Int. Cl.$^6$ ............................................. G01N 21/17
[52] U.S. Cl. ...................................... 436/79; 436/171
[58] Field of Search ..................... 436/73, 79, 171; 422/86

[56] References Cited

U.S. PATENT DOCUMENTS

| | | | |
|---|---|---|---|
| 4,994,395 | 2/1991 | Chapoteau et al. | 436/79 |
| 5,145,787 | 9/1992 | Chapoteau et al. | 436/79 |
| 5,187,103 | 2/1993 | Czech et al. | 436/79 |
| 5,188,802 | 2/1993 | Schaeffer et al. | 422/56 |
| 5,219,679 | 6/1993 | Abraham et al. | 429/192 |
| 5,290,702 | 3/1994 | Chang | 436/2 |
| 5,290,704 | 3/1994 | Chang | 436/128 |
| 5,304,436 | 4/1994 | Chang | 429/194 |

OTHER PUBLICATIONS

Solving Problems in Analytical Chemistry, by Stephen Brewer, Catalogued 1941, copyright John Wiley & Sons 1980 pp. 271-285.

*Primary Examiner*—Robert J. Warden
*Assistant Examiner*—N. Bhat
*Attorney, Agent, or Firm*—Charles Jew

[57] ABSTRACT

An optical absorbance method for the quantitative determination of Lewis acid decomposition products in nonaqueous electrolytes.

8 Claims, 3 Drawing Sheets

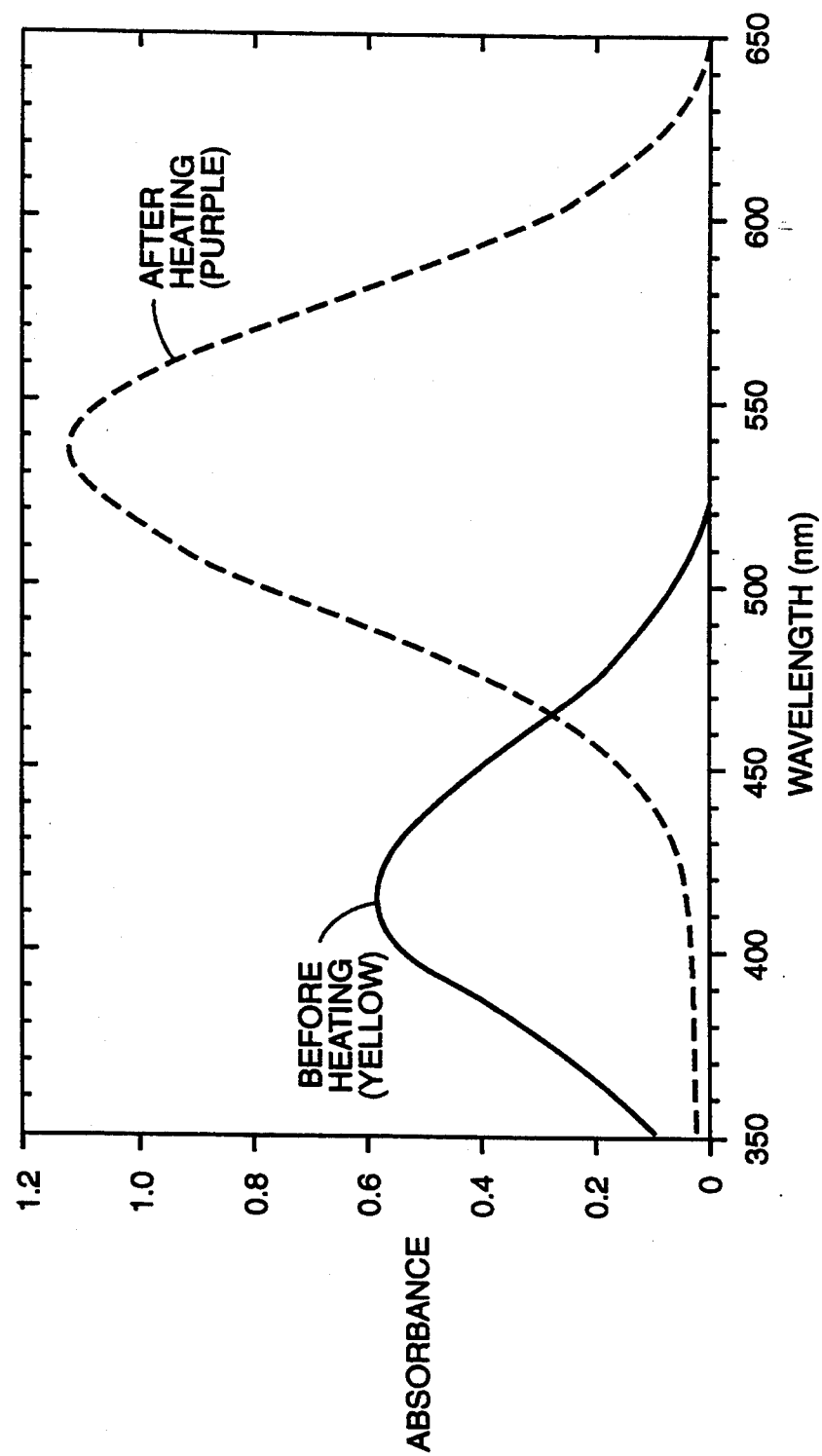
FIG._1

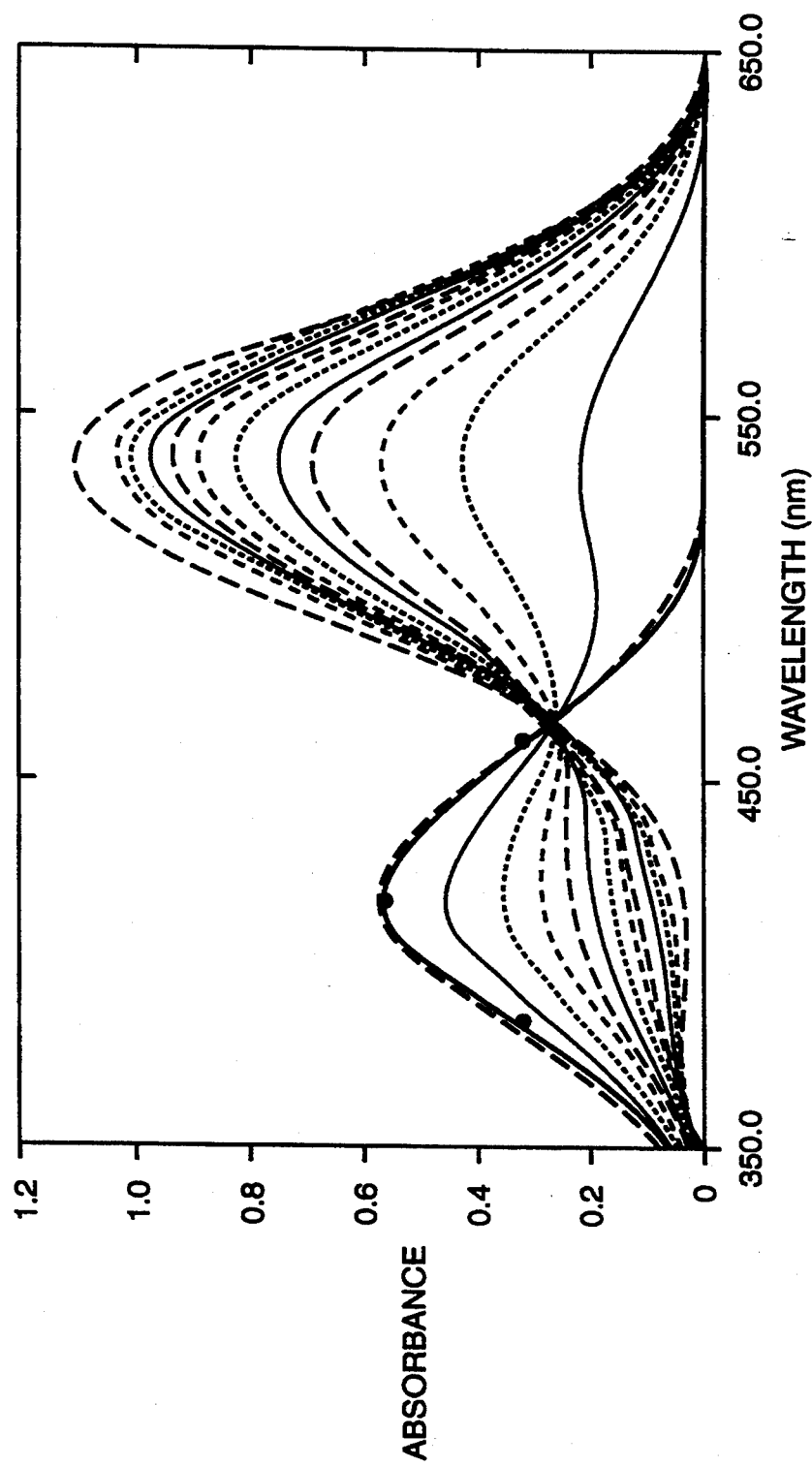
FIG._2

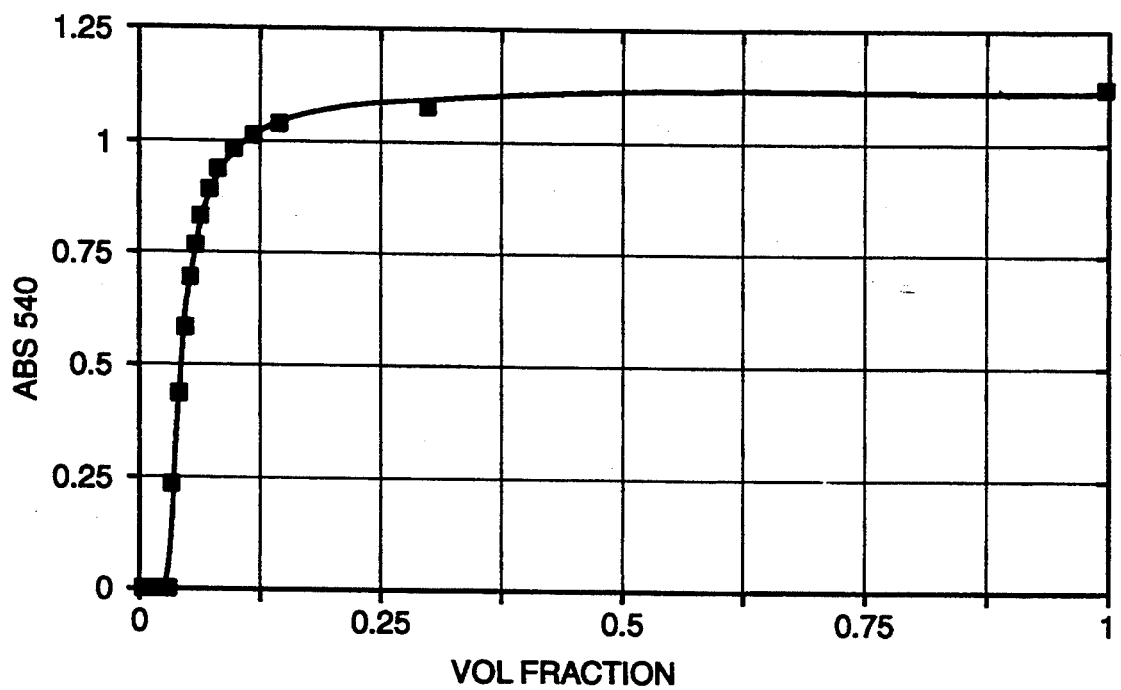
FIG._3
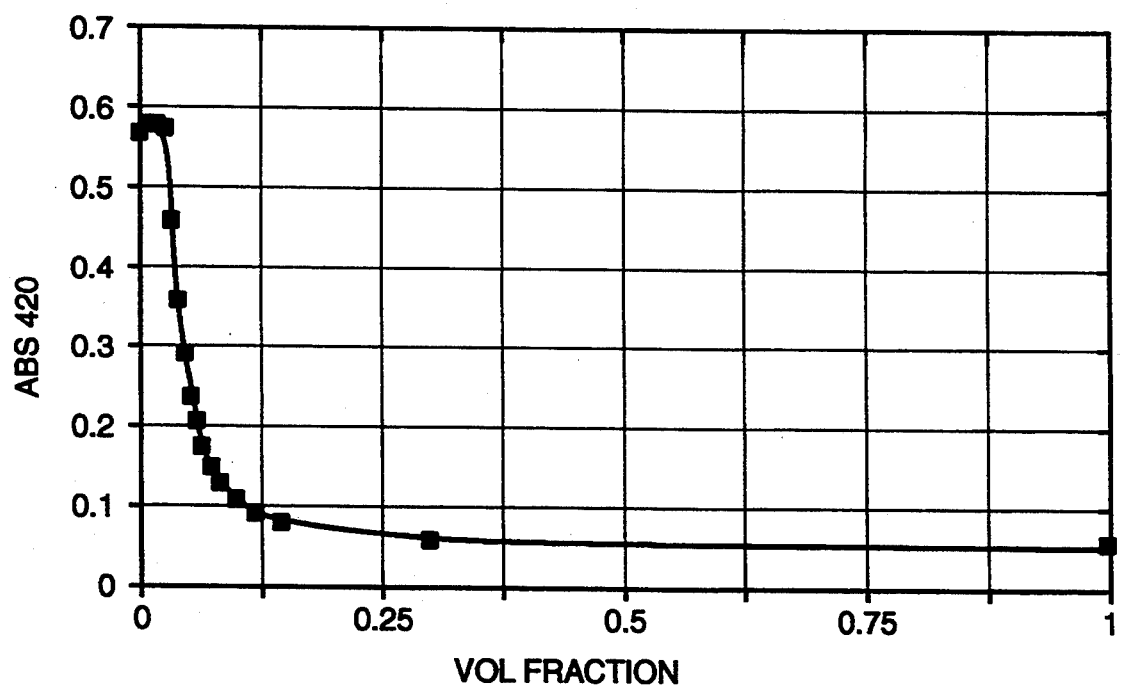
FIG._4

METHOD TO DETECT LEWIS ACID DECOMPOSITION PRODUCTS IN LITHIUM SALT-CONTAINING NONAQUEOUS ELECTROLYTE

FIELD OF THE INVENTION

This invention relates to a novel quantitative method for the determination of Lewis acid impurities in non-aqueous electrolytes. Non-aqueous electrolytes find extensive use in solid electrochemical batteries. Lithium salts are used in the solid non-aqueous electrolyte of solid lithium electrochemical batteries.

BACKGROUND OF THE INVENTION

Electrochemical cells containing an anode, a cathode and a solid, solvent-containing electrolyte are known in the art and are usually referred to as "solid batteries". These cells offer a number of advantages, including improved safety features. Notwithstanding their advantages, the use of certain of the solid state batteries over repeated charge/discharge cycles may be substantially impaired when they exhibit significant drops in their charge and discharge capacity over repeated cycles, as compared to their initial charge and discharge capacity, due to the decomposition of the solid electrolyte. Specifically, solid batteries employ a solid electrolyte interposed between a cathode and a anode. The solid electrolyte contains either inorganic or an organic matrix as well as a suitable inorganic ion salt. The inorganic matrix may be nonpolymeric or polymeric, whereas the organic matrix is typically polymeric. Suitable organic polymeric matrices are well known in the art and are typically organic polymers obtained by polymerization of a suitable organic monomer as described, for example, in U.S. Pat. No. 4,908,283. Suitable organic constituents include, by way of example, polyethylene oxide, polypropylene oxide, polyethylene imine, polyepichlorohydrin, polyethylene succinate, and an acryloyl-derivatized polyalkylene oxide containing an acryloyl group of the formula, $CH_2=CR'C(O)O-$ where $R'$ is hydrogen or a lower alkyl of from 1 to 6 carbon atoms.

Electrochemical cells containing a solid electrolyte, i.e., a polymeric matrix, may suffer from low ion conductivity and accordingly, in order to maximize the conductivity of these materials, the matrix is generally constructed into a very thin film, i.e., on the order of about 25 to 250 $\mu$m. It is apparent, the reduced thickness of the film, reduces the total amount of internal resistance within the electrolyte thereby minimizing losses in conductivity due to internal resistance. However, the solid electrolyte also may contain a solvent (plasticizer) which is typically added to the matrix in order to enhance the solubility of an inorganic ion salt in the solid electrolyte and thereby increase the conductivity of the electrochemical cell.

Suitable solvents, well-known in the art for use in such solvent electrolytes, include by way of example, propylene carbonate, ethylene carbonate, $\gamma$-butyrolactone, tetrahydrofuran, glyme (dimethoxyethane), diglyme, triglyme, tetraglyme, dimethylsulfoxide, dioxolane, sulfolane, and the like.

In a method of forming the solid electrolyte, a monomer or partial polymer of the polymeric matrix to be formed is combined with appropriate amounts of the inorganic ion salt and the solvent. This mixture is then placed on the surface of a suitable substrate (e.g., the surface of the cathode) and the monomer is polymerized or cured (or the partial polymer is then further polymerized or cured) by conventional techniques such as heat, ultraviolet radiation, electron beams, etc. so as to form the solid, solvent-containing electrolyte.

When the solid electrolyte is formed on a cathodic surface, an anodic material can then be laminated onto the solid electrolyte to form a solid electrochemical cell.

A battery may exhibit a decline in capacity over its lifetime due to decomposition of the inorganic salts present in the solid electrolyte.

For example, $LiPF_6$ is a typically preferred inorganic salt finding use in solid electrolytes of lithium-containing electrochemical cells. $LiPF_6$ is known to undergo thermal decomposition at temperatures within the operating range of rechargeable lithium batteries. Decomposition products shorten the battery lifetime and interfere with its operation.

The prior art does not contain a satisfactory method for the quantitative determination of $LiPF_6$ decomposition products in nonaqueous media.

It would be advantageous to develop a sensitive method for detecting and quantifying the decomposition of lithium salts such as $LiPF_6$ and its decomposition product(s) in non-aqueous electrolytes. It would then be possible to study methods of inhibiting decomposition in the environment of the electrolyte.

Difficulties are presented in the determination of the decomposition products, of an acid character, in non-aqueous solvents. The use of colored pH indicators in aqueous solutions is well known. However, the concept of pH is not considered relevant in non-aqueous solvents. Consequently, it is not possible to make a direct measurement of acid content in non-aqueous solvent by the use of ordinary water soluble pH indicators.

Furthermore, the classic definition of "acid" is that of a proton donor, and the classic definition of a "base" is that of a proton acceptor. The classic definition of an acid-base indicator is that of a chemical moiety which substantially changes its absorption spectrum in the ultraviolet or visible portion of the spectrum upon acceptance and release of a proton.

The concept of acid and base has been generalized. A generalized acid definition includes Lewis acids and Lewis bases. The Lewis acid is defined as that chemical moiety which accepts an electron pair, and a Lewis base is that chemical moiety which donates an electron pair. Consequently, indicators for non-aqueous Lewis acid-base equilibria are not the same chemical compounds which find use as indicators for hydrogen ion acid-base equilibria in water.

SUMMARY OF THE INVENTION

The present invention is directed to the discovery of the method of quantitatively determining the concentration of lithium salt decomposition products in non-aqueous electrolytes. If the total concentration of Lewis acid impurities is denoted as $[A]_o$, then the method comprises the steps of:

(a) Mixing a measured portion of the electrolyte containing the Lewis acid impurities with a measured amount of a compatible Lewis base azo dye, denoted Id, to form a solution of said azo dye in the electrolyte. The equilibrium concentrations of the Lewis acid impurity, $[A]$, and the equilibrium concentration of the Lewis base azo dye, $[Id]$, are related by the equilibrium constant $K=[AId]/[A]$·

[Id], where [AId] is the concentration of the reaction product of A and Id.

(b) Measuring the absorbance, $AB(\lambda_{Id})$ of said solution at the peak absorbance wavelength, $\lambda_{Id}$, of Id and the absorbance of the solution, $AB(\lambda_{AId})$, at the peak absorbance wavelength, $\lambda_{AId}$, of AId.

(c) Calculating the concentration [AId] from the relation $[AId] = AB(\lambda_{AId})/\epsilon(\lambda_{AId})$ where $(\lambda_{AId})$ is the absorptivity of $\lambda_{AId}$.

(d) Calculating the concentration [Id] from the relation $[Id] = AB(\lambda_{Id})/\epsilon(\lambda_{Id})$ where $\epsilon(\lambda_{Id})$ is the absorptivity of Id at $\lambda_{Id}$.

(e) Calculating the concentration of Lewis acid impurities in the solution from the relationship $[A]_o = -[AId] + [AId]/K[Id]$.

Wherein a preferred embodiment, the quantities K, $\epsilon(\lambda_{Id})$ and $\epsilon(\lambda_{AId})$ are determined from the empirical relationship between $AB(\lambda)$ and the volume fraction of heated electrolyte in a mixture of heated and unheated electrolyte.

The non-aqueous electrolytes finding use within the scope of the present invention include organic carbonates, such as linear aliphatic carbonates, cyclic aliphatic carbonates, butylene carbonate, propylene and ethylene carbonate, dioxolanes, dimethylsulfoxide, sulfolane, methyltetrahydrofuran, dioxanes, taken alone or in mixtures with glyme, diglyme, triglyme, etc. polyalkylene oxides, such as polyethylene oxide, polypropylene oxide, ethoxylated trimethyl-propane triacrylate, epichlorohydrin, acryloyl-derivatized polyalkylene oxide, vinyl sulfonate polyalkylene oxide, polymer precursors known to the art to be non-aqueous solid electrolyte forming materials, and having non-substantial optical absorptivity in the regions of the spectrum where the acid and base forms of the azo dye indictor absorb.

Typical azo dyes finding use within the scope of the present invention include tropeaolin, metanil yellow, mordant orange, methyl orange, and methyl red.

Lithium salts whose decomposition products are quantitatively determinable by the method of the present invention include $LiPF_6$, $LiAsF_6$, $LiBF_4$, and the like.

BRIEF DESCRIPTION OF THE DRAWINGS

FIG. 1 illustrates the spectra of heated and unheated $LiPF_6$ electrolyte with metanil yellow.

FIG. 2 illustrates the spectra of mixtures of heated and unheated $LiPF_6$ electrolyte with metanil yellow as the volume fraction of the heated electrolyte varied from 0.00 to 0.14.

FIG. 3 illustrates the optical absorbance at 540 nm of electrolyte containing metanil yellow as a function of the fraction of heated electrolyte present.

FIG. 4 illustrates the optical absorbance at 420 nm of electrolyte containing metanil yellow as a function of the fraction of heated electrolyte present.

DETAILED DESCRIPTION OF PREFERRED EMBODIMENTS

Prior to describing this invention in further detail the following terms will first be defined.

Definitions

As used herein, the following terms have the following meanings.

The term "non-aqueous electrolyte" refers to any component of the uncured non-aqueous mixture, which upon curing becomes a solid electrolyte for use in electrochemical cells. Such materials include mixtures of a solid matrix forming monomer, a solvent, including mixtures of solvents, and an inorganic ion salt or mixtures of such salts.

The term "a solid matrix forming monomer" refers to inorganic or organic materials which in monomeric form can be polymerized, preferably in the presence of an inorganic ion salt and a solvent mixture to form solid matrices which are suitable for use as solid electrolytes in electrochemical cells. Suitable solid matrix forming monomers are well-known in the art and the particular monomer employed is not critical. Preferably, the solid matrix forming monomers have at least one hetero-atom capable of forming donor acceptable bonds with inorganic cations (e.g., alkali ions). When polymerized, these compounds can form an ionically conductive matrix.

Examples of suitable organic solid matrix forming monomers include, by way of example, propylene oxide, ethylene imine, ethylene oxide, epichlorohydrin, acryloyl-derivatized polyalkylene oxides, vinyl sulfonate polyalkylene oxides, polyurethane acrylate, and the like, as well as mixtures thereof.

The term "inorganic ion salt" refers to any inorganic salt which is suitable for use in a solid electrolyte. The particular inorganic ion salt employed is not critical in examples of suitable inorganic ion salts include, $LiClO_4$, $LiI$, $LiSCN$, $LiBF_4$, $LiAsF_6$, $LiCF_3$, $LiPF_6$, $NaI$, and $NaSCN$.

The term "solvent" refers to the heretofore mentioned non-aqueous solvent or "plasticizers" typically containing no more than about 12 carbon atoms, and not containing a hydroxyl group. Preferred are the organic carbonates and the glymes, and mixtures thereof.

The term "electrochemical cell" refers to a composite containing an anode, a cathode, and ion-conducting electrolyte interposed there between.

The term "empirical" in the context of the present invention denotes a method based on an observable relationship. For example, fitting a curve to observed data points, by methods well known to the art, in order to obtain the values of parameters in a mathematical or theoretical relationship is an empirical method.

The term "Lewis base azo dye" refers to materials containing one or more —N=N— (i.e. azo compounds), preferably containing the "azo benzene" group R—$\phi$—N=N—$\phi$—R', wherein —$\phi$— is a phenylene group, and wherein R is a substituent or a substituted aryl, diaryl, or triaryl moiety. Such substituents are selected from amino, nitro, alkyl, hydroxy, halogen, carboxyl, alkenyl, alkylene and $SO_3$ substituents; and R' is such a substituent, or is a substituted aryl, diaryl or triaryl group. Most azo dyes are carboxylic or sulfonic acids or their salts. Azo dyes are prepared by coupling a diazotized aromatic amine (such as $[ArN_2]Cl$, where Ar is an aromatic residue) with a phenol or an aromatic amine. In the aforementioned preferred Lewis base azo dyes, coupling takes place para to the hydroxyl or amino group, or ortho if the para position is occupied. Examples of azo compounds include sodium 2-sulfonate-4,4'-dinitro-azobenzene; 4'-nitro-azobenzene; 1-naphthalene-azobenzene; sodium 4-sulfonate-4'-diphenylamino-azobenzene (tropaeolin); 4-hydroxy-5-carboxy-4'-nitro-azobenzene (mordant orange); sodium 6-carboxylate-4'-dimethylamino-azobenzene (methyl red); sodium 5-sulfonate-4'-phenylamino-azobenzene (metanil yellow); and sodium 4-sulfonate-4'-dimethylamino-azobenzene (methyl orange).

The azo dyes and their chemical action is disclosed by Noller, "Chemistry of Organic Compounds", Saunders Company, Philadelphia, 1965, pp. 743-775 which disclosure is incorporated herein by reference in its entirety. Particularly preferred is metanil yellow although other Lewis base azo dyes such as methyl orange and methyl red may be used.

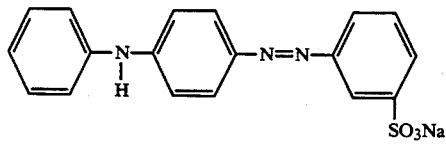

METANIL YELLOW

The Lewis base azo dye exists in two forms within the purview of this invention. As the Lewis base it is represented as Id and as the "neutralized" form in the presence of a Lewis acid, which itself is represented as A, the azo dye is represented as AId. AId is believed to be a complex of the Lewis acid impurity with the azo dye Lewis base. Consequently, there exists an equilibrium, $A + Id = AId$.

Both Id and AId must have easily measureable and different absorption spectra in the presence of the electrolyte, or any component thereof. Consequently, metanil yellow is the preferred Lewis base azo dye, since it satisfies this requirement. Surprisingly, methyl orange and methyl red showed only small spectral differences in the base (Id) and neutralized (AId) forms. Surprisingly, tropaeolin did not show any significant spectral difference in the presence of the Lewis acid.

The term "[A], [Id] and [AId]" denote the equilibrium concentration in moles per liter (M) for the respective species in the non-aqueous electrolyte, in the presence of the Lewis base, Id.

The term "$[A]_o$" denotes the total concentration of Lewis acid in the electrolyte. $[A]_o = [A] + [AId]$.

The term $[Id]_o$ denotes the total concentration of Lewis base azo dye in the electrolyte. $[Id]_o = [Id] + [AId]$.

The terms "$\lambda_{Id}$" and "$\lambda_{AId}$" denote the peak spectral absorbance wavelengths of the species Id and AId, respectively, expressed in nm of wavelength.

The term "$AB(\lambda)$" denotes the absorbance at wavelength $\lambda$.

The terms "$AB(\lambda_{Id})$" and "$AB(\lambda_{AId})$" denote the absorbance of the species Id and AId, respectively, at their peak spectral absorbance, plus any background absorbance at those wavelengths from other sources. Such background absorbance is denoted "$B(\lambda_{Id})$" and "$B(\lambda_{AId})$", respectively.

The terms "$\epsilon(\lambda_{Id})$" and "$\epsilon(\lambda_{AId})$" denote the specific absorbance or molar absorptivity of the species Id and AId, respectively, at wavelength $\lambda_{Id}$ and $\lambda_{AId}$, respectively. Consequently, it is evident that, for example, $AB(\lambda_{Id}) = \epsilon(\lambda_{Id})[Id] + B(\lambda_{Id})$.

The term "K" represents the equilibrium constant of the reaction $A + Id = AId$. $K = [AId]/[A][Id]$ and $K = [AId]/([A]_o - [AId])([Id]_o - [AId])$. The latter equation can be solved for [AId].

Similarly, $K = ([Id]_o - [Id])/(([A]_o + [Id] - [Id]_o)[Id])$, an equation which can be solved for [Id].

The expressions for [AId] and [Id] are then related to the observed absorbance by $AB(\lambda_{Id}) = \epsilon(\lambda_{Id})[Id] + B(\lambda_{Id})$ and $AB(\lambda_{AId}) = \epsilon(\lambda_{AId})[AId] + B(\lambda_{AId})$.

Methodology

The unknown quantities in the expressions for $AB(\lambda_{Id})$ and $AB(\lambda_{AId})$ are $\epsilon(\lambda_{Id})$, $\epsilon(\lambda_{AId})$, K and $[A]_o$. By measuring $AB(\lambda_{Id})$ and $AB(\lambda_{AId})$ at various equilibrium concentrations of A expressed as the volume fraction of heated electrolyte in a mixture of heated and unheated electrolyte (at constant total dye concentration, $[Id]_o$), one obtains the relationships illustrated by the data points in FIGS. 3 and 4. By fitting the data points to the curves, the aforementioned unknown quantities are determined with surprisingly high consistency and precision.

The method will be described in terms of LiPF6 decomposition, for which one such possible reaction is $LiPF_6 \rightarrow LiF + PF_5$, wherein $PF_5$ is one such Lewis acid impurity determinable by the present method. The reaction is accelerated by heat and is not reversible.

The challenge posed by such decompositions is how to detect the Lewis acid, in very low concentrations, in non-aqueous media.

$LiPF_6$ in a mixture of propylene carbonate and triglyme electrolyte was prepared. The azo dye was added to a portion of the fresh electrolyte and the visible-ultraviolet spectrum recorded. Then the electrolyte (without the dye) was heated for three hours at 80° C. and cooled to room temperature. The azo dye was added in an aliquot of the heated electrolyte and the spectrum recorded. The spectra were compared.

When the azo dye is metanil yellow, FIG. 1 shows the result of recording the spectra of heated and unheated electrolyte. FIG. 2 shows the spectra of mixtures of heated and unheated electrolyte in different proportions. The unheated electrolyte with metanil yellow shows $\lambda_{Id} = 420$ nm. The heated electrolyte with metanil yellow shows $\lambda_{AId} = 540$ nm. The metanil yellow was added to the electrolyte in a concentration of $1.73 \times 10^{-5}$M. The concentration of $LiPF_6$ in the electrolyte was 1.0M.

The data points in FIG. 3 and FIG. 4 show the conversion of the data of FIG. 2 into the absorbance of the azo dye-containing heated and unheated electrolyte mixture at $\lambda_{Id}$ and $\lambda_{AId}$, respectively, as a function of the volume fraction of heated electrolyte in the mixture.

From the equilibrium relationship, an empirical fit of the data at $\lambda_{Id}$ and at $\lambda_{AId}$ was used to determine the values of K, $\epsilon(\lambda_{Id})$ and $\epsilon(\lambda_{AId})$. The empirical fit is shown by the solid lines in FIGS. 3 and 4. Table I shows the values obtained. The ranges denote 99% confidence limits.

TABLE I

|  | $\epsilon(\lambda_{AId})$ | $\epsilon(\lambda_{Id})$ | K (m$^{-1}$) |
|---|---|---|---|
| From data at 540 nm | 65250 ± 860 |  | 1.2 ± .5 × 10$^5$ |
| From data at 420 nm |  | 30450 ± 560 | 1.7 ± .6 × 10$^5$ |

EXAMPLES

A metanil yellow stock solution was prepared by dissolving 10 mg of the dye in 7 ml of methanol. The dye concentration was $3.81 \times 10^{-3}$M. The dye solution can be kept for more than three months. 10 μl of the dye solution was added to a 1 cm cuvette with a stopper. The solvent, methanol, was removed by heating the cuvette in an oven. The amount of dye added was $3.81 \times 10^{-8}$ mole. The exact amount of dye is not critical. 2 ml of electrolyte to be analyzed was added to the cuvette. The electrolyte contained the inorganic salt $LiPF_6$. The contents of the cuvette were mixed well. The dye concentration in the cuvette was about $1.91 \times 10^{-5}$M. The exact concentration is not critical. The absorbance was measured at 540 and at 420 nm. For highest accuracy, $AB(\lambda_{540})$ should be smaller than $2 \times AB(\lambda_{420})$. If $AB(\lambda_{540}) > 2 \times AB(\lambda_{420})$, the electrolyte is diluted with pure solvent and the preceding steps are repeated until $AB(\lambda_{540})$ is less than $2 \times AB(\lambda_{420})$. The dilution factor is needed in the final calculation.

The concentration of AId and Id was calculated using the relationships $[AId] = AB(\lambda_{540})/65250$, and $[Id] = AB(\lambda_{420})/30450$. The numbers 65250 and 30450 are the molar absorptivities of the two forms of the dye at 540 and 420 nm. The concentrations are given in M. The concentration of the Lewis acid impurity in the solution was calculated using the relationships $[A]_o = [AId] + 7.1 \times 10^{-6} \times [AId]/[Id]$. $7.1 \times 10^{-6}$ is the average reciprocal of the equilibrium constant of the reaction $A + Id = AId$. Applying the dilution factors, the concentration of the Lewis acid in the original sample was calculated.

The method of this invention is consistent and precise. For example, an electrolyte mixture of propylene carbonate and triglyme containing 1.0M $LiPF_6$ was divided into an unheated portion maintained at room temperature and a portion heated at 80° C. for 30 min., then cooled to room temperature. When the volume fraction of heated electrolyte in the mixture of heated and unheated electrolyte was 0.0385, the total concentration of Lewis acid, $[A]_o$, was found to be $1,063 \times 10^{-3}$M in good agreement with the predicted value of $1.11 \times 10^{-3}$M.

While the invention has been described in terms of various preferred embodiments, the skilled artisan will appreciate the various modifications, substitutions, omissions and changes which may be made without departing from the spirit hereof. The descriptions of the subject matter in this disclosure are illustrative of the invention and are not intended to be construed as limitation upon the scope of the invention.

What is claimed is:

1. A method of quantatively determining the concentration of lithium salt Lewis acid impurities, $[A]_o$, in a non-aqueous electrolyte comprises the steps of:
   (a) Mixing a measured portion of said electrolyte containing said Lewis acid impurities with a measured amount of compatible Lewis base azo dye, Id, to form a solution of said azo dye in said electrolyte, wherein the equilibrium concentrations of said Lewis acid impurity, [A], and the equilibrium concentration of said Lewis base azo dye, [Id], are related by the empirically determined equilibrium constant, K, where $K = [AId]/[A][Id]$, and [AId] is the concentration of the reaction product of A and Id;
   (b) Measuring the absorbance, $AB(\lambda_{Id})$, of said solution at the peak absorbance wavelength, $\lambda_{Id}$, of Id and the absorbance of said solution, $AB(\lambda_{AId})$, at the peak absorbance wavelength, $\lambda_{AId}$, of AId;
   (c) determining the concentration of [AId] from the relation $[AId] = AB(\lambda_{AId})/\epsilon(\lambda_{AId})$, where $\epsilon(\lambda_{AId})$ is the absorptivity of AId at $\lambda_{AId}$;
   (d) determining the concentration of [Id] from the relation $[Id] = AB(\lambda_{Id})/\epsilon(\lambda_{Id})$ where $\epsilon(\lambda_{Id})$ is the absorptivity of Id at $\lambda_{Id}$; and
   (e) determining the concentrating of Lewis acid impurities in said solution from the relationship $[A]_o = [AId] + [AId]/K[Id]$.

2. A method according to claim 1 wherein said azo dye is selected from the group consisting of methyl orange, methyl red and metanil yellow.

3. A method according to claim 1 wherein said non-aqueous electrolyte comprises organic materials selected from the group consisting of organic carbonates, glymes, polyethers, aprotic solvents and mixtures thereof.

4. A method according to claim 1 wherein said non-aqueous electrolyte comprises mixtures of triglyme and propylene carbonate.

5. A method according to claim 1 wherein if $AB(\lambda_{AId})$ is greater than twice $AB(\lambda_{Id})$, the electrolyte is diluted with solvent, and additional dye is added until $AB(\lambda_{AId})$ is less than twice $AB(\lambda_{Id})$.

6. A method according to claim 1 wherein said azo dye is metanil yellow.

7. A method according to claim 1 wherein said lithium salt is $LiPF_6$.

8. A method according to claim 1 wherein the quantities K, $\epsilon(\lambda_{Id})$ and $\epsilon(\lambda_{AId})$ are determined from the empirical relationship between $AB(\lambda)$, $AB(\lambda_{AId})$ and the volume fraction of heated electrolyte in a mixture of heated and unheated electrolyte.

* * * * *